United States Patent
Schuster et al.

(10) Patent No.: US 6,510,334 B1
(45) Date of Patent: Jan. 21, 2003

(54) METHOD OF PRODUCING AN ENDOPROSTHESIS AS A JOINT SUBSTITUTE FOR A KNEE JOINT

(76) Inventors: Luis Schuster, München (DE); Christoph Schuster, München (DE)

(*) Notice: Subject to any disclaimer, the term of this patent is extended or adjusted under 35 U.S.C. 154(b) by 231 days.

(21) Appl. No.: 09/712,728

(22) Filed: Nov. 14, 2000

(51) Int. Cl.[7] .............................. A61B 6/00; A61F 2/28
(52) U.S. Cl. ..................... 600/407; 600/425; 128/920
(58) Field of Search ................ 600/407, 410, 600/425; 128/920; 378/901

(56) References Cited

U.S. PATENT DOCUMENTS

| | | | |
|---|---|---|---|
| 4,704,686 A | * 11/1987 | Aldinger | 700/163 |
| 5,370,692 A | * 12/1994 | Fink et al. | 128/898 |
| 5,677,855 A | 10/1997 | Skeeters et al. | |
| 5,682,886 A | 11/1997 | Delp et al. | |
| 5,798,924 A | * 8/1998 | Eufinger et al. | 700/117 |
| 5,824,085 A | * 10/1998 | Sahay et al. | 128/898 |
| 5,871,018 A | 2/1999 | Delp et al. | |

FOREIGN PATENT DOCUMENTS

| | | |
|---|---|---|
| DE | 3213434 | 10/1983 |
| DE | 3522196 | 2/1986 |
| DE | 3626549 | 2/1988 |
| DE | 4304572 | 8/1994 |
| DE | 4341367 | 6/1995 |
| DE | 4434539 A1 | 4/1996 |
| DE | 4434539 C2 | 6/1998 |
| DE | 19726618 | 12/1998 |

* cited by examiner

Primary Examiner—Joseph Pelham
(74) Attorney, Agent, or Firm—Ostrolenk, Faber, Gerb & Soffen, LLP

(57) ABSTRACT

In a method of producing an endoprosthesis as an joint substitute for knee joints three-dimensional femoral and tibial components of the endoprosthesis are prepared in combination with three-dimensional femoral and tibial components of an associated implantation aid on the basis of respective visual patterns that are derived from virtually altering a preoperative tomographic image of a damaged knee joint.

11 Claims, 5 Drawing Sheets

METHOD OF PRODUCING AN ENDOPROSTHESIS AS A JOINT SUBSTITUTE FOR A KNEE JOINT

FIELD OF THE INVENTION

This invention relates to a method of producing an endoprosthesis as a joint substitute for knee joints. The invention further also relates to an operative set for carrying out operations on damaged knee joints utilising an endoprosthesis which is produced in accordance with the method of this invention.

BACKGROUND OF THE INVENTION

A surgical intervention on a knee joint is usually taken into consideration by the attending physician when the patient complains about severe pains in the knee and disabilities as a consequence of, e.g., rheumatoid arthritis or other joint diseases. The surgical intervention conventionally takes place in a plurality of steps for obtaining an adaption to the shape of industrially manufactured joint moldings. Such moldings are presented in different graduated sizes and with different designs for being ultimately fitted to surfaces of the knee joint as prepared, e.g., by using an oscillating sawing blade and mainly provided for the anterior femoral condyle, the distal femur, the proximal tibia and the patella. The surfaces are provided in such a way that a vertical alignment is achieved for the multiple components of the associated endoprosthesis in relation to an axis which is obtained, e.g., by means of a preoperative X-ray image and an intramedullary pin align system for the straight line connecting the center of the hip, the knee and the malleolus. An illustrative representation of such a surgical procedure is described, e.g., in U.S. Pat. No. 4,759,350 (incorporated by referenece) by a reference also to a specific intramedullary pin system.

The implantation of such multiple knee joint endoprostheses is very time consuming and often results only in an approximate toration of the conditions of a healthy knee joint when taking into consideration existing differences in the patient's growth. Complications therefore often occur which must be attributed to the mechanics of the implanted components of the endoprosthesis whereby such complications may lead, e.g., to an anterior knee joint pain syndrome which is caused by an incorrect gliding of the patella with a nonphysiological loading of the femur-patella gliding joint. Irritations also frequently develop, occasionally with considerable hypertrophy of the joint mucosa and pronounced effusions in the knee joint as a consequence of a massive abrasion of the implanted endoprosthesis components, some of which may consist of polyethylene and will then lead to an unfavourable gliding behaviour if such abrasion becomes excessive. Loosening of the bone anchoring of these components may also occur so that it is frequently necessary to implant a new endoprosthesis.

For avoiding such complications as often accompanied by a repeated implantation of a new endoprosthesis with the requirement for a resection of further bone parts there has already been proposed by one of the present inventors a method as described in U.S. Pat. No. 5, 735, 277 (incorporated by reference) according to which still prior to a surgical intervention on a knee joint a preoperative tomographic image of the damaged knee joint is prepared by means either of a computed tomography or by means of a nuclear spin resonance tomography. In accordance with this known method there is further prepared a healthy knee joint tomographic image for which the contours of at least the femoral bone and of the tibia of the damaged knee joint are approximated to those of a healthy knee joint. Afterwards a postoperative tomographic image of the damaged knee joint is prepared for enabling by comparison a determination of the differences between the contours of at least the femoral bone and of the tibia of the healthy knee joint tomographic image and the contours of at least the femoral bone and of the tibia of the postoperative tomographic image of the damaged knee joint. Such a comparison therefore allows a subsequent preparation of a tomographic reference image which accordingly represents those differences. This tomographic reference image finally forms the basis for preparing at least a femoral component and a tibial component of an endoprosthesis which may be used in connection with the factual surgical intervention on the damaged knee joint of which the preoperative tomographic image has been prepared.

Since with this known method a tomographic reference image representing differences between a preoperative tomographic image and a postoperative tomographic image of the damaged knee joint is used as a basis for preparing the components of an endoprosthesis this method could include a multiple error rate in respect to the preparation of such a reference image as caused, e.g., by the preparation of the postoperative tomographic image and further by the determination of the differences that will exist between the postoperative tomographic image and the tomographic image of a healthy knee joint which, e.g., will be prepared by either manually altering the preoperative tomographic image or by preparing a mirror image of a healthy knee joint of the patient. The preparation of such a tomographic reference image of course also raises the computer-oriented assistance for the preparation of an endoprosthesis in accordance with this known method.

SUMMARY OF THE INVENTION

An object of the present invention is therefore to provide a method of producing an endoprosthesis as a joint substitute for knee joints which minimises the error rate in connection with a surgical intervention on a damaged knee joint and which further optimizes the surgical intervention in respect of the possibility to allow a very close adaption at least of the femoral and tibial components of an endoprosthesis to the contours of the bone joints as specifically prepared on respective surfaces during a surgical intervention for snugly fitting thereto the components of the endoprosthesis.

A further object of the present invention relates to the provision of an operative set for carrying out operations on damaged knee joints which will allow a practically ready-made surgical intervention on a damaged knee joint as accompanied with less pain for the patient.

DESCRIPTION OF THE INVENTION

In accordance with a preferred embodiment of the present invention a method of producing an endoprosthesis as a joint substitute for knee joints is started by preparing a preoperative tomographic image of the damaged knee joint. The tomographic image could be prepared either by a computed tomography or by a nuclear spin resonance tomography which allows to define very sharp contours of the damaged knee joint as a correspondingly optimal precondition for all of the subsequent steps of this method.

The tomographic image of the damaged knee joint is then virtually altered for approximating the contours of at least the femoral bone and of the tibia of the damaged knee joint to the contours of a healthy knee joint. This virtual alteration should preferably exemplified with a stretched condition of the knee allowing a precise plotting of the rear and lower joint surface of the femoral bone and of the entire shinbone surface of the tibia to thereby obtain more or less ideal contours for the fitting of the endoprosthesis during the factual surgical intervention as later carried out. This step of virtually altering the preoperative tomographic image may be exemplified manually or may alternatively be exemplified by the preparation of a mirror image of a healthy knee joint of the patient. It may also be prepared by identifying an image of a healthy knee joint having contours of the femoral bone and of the tibia comparable to the contours of the preoperative image of the damaged knee joint.

The altered femoral and tibial components defining therefore respective components of a healthy knee joint are subsequently virtually severed as respectively visual patterns for the endoprosthesis. The severing is carried out on marked severing areas which later serve as thusly predetermined severing areas for severing the associated components of the damaged knee joint from the joint bones during the factual operation of the damaged knee joint. The severing is carried out on the femoral bone of the damaged knee joint preferably with three different severing areas and on the tibia with one or with two different severing areas. By this virtual severing visual patterns are therefore obtained which are directly oriented in respect to the damaged knee joint and thusly allow a preparation of femoral and tibial components of an endoprosthesis which exactly correspond to the femoral and tibia components as altered by the preceding step of virtually altering the preoperative tomographic image of the damaged knee joint. The different severing areas as marked for this virtual severing step could preferably also be supplemented virtually with anchoring means such as, e.g., pegs for the three-dimensional components of the endoprosthesis when later fitted to the resection areas of the joint bones. Such pegs when exemplified would then be intended for being fitted snugly into associated peg holes of the corresponding resection areas of the joint bones.

This marking of severing areas is also used for virtually preparing tomographic images of femoral and tibial templates for the femoral and tibial components of the damaged knee joint as corresponding separate visual patterns of an implantation aid which by virtually transferring the marked severing areas for the preparation of such templates will therefore fit snugly to the damaged knee joint. As in case of the preparation of the femoral and tibial components of the endoprosthesis the virtually prepared tomographic image of such femoral and tibial templates may directly be used for the preparation of the associated implantation aid. The marked severing areas showing up on the templates are transferred to the corresponding components of the implantation aid and serve as corresponding guiding slots of a guide aid for guiding, e.g., an oscillating sawing blade during the factual operation of the damaged knee joint when the damaged knee joint components are then factually severed from the joint bones. When preparing the virtual image of the femoral and tibial templates it is therefore essential that the implantation aid and therefore in the first place the femoral and tibial templates receive a very exact positioning on the damaged knee joint so that with the oscillating sawing blade correspondingly exact resection surfaces will be obtained on the joint bones for fitting snugly to the associated surfaces of the femoral and tibial components of the endoprosthesis for which the marked severing areas have been virtually transferred for the preparation of such templates. It should therefore be preferred to design such templates and therefore also their corresponding implantation aids, e.g., in the form of caps for obtaining an enveloping of the severing areas which therefore identify negative images of the resection areas as provided by the sawing blade on the associated joint bones.

The visual patterns of both the femoral and tibial components of the endoprosthesis and the femoral and tibial components of the associated implantation aid are then used for preparing corresponding three-dimensional parts. Such a conversion could be exemplified by means of the so-called "Rapid Prototyping" (incorporated by reference) according to which there are obtained so-called STL patterns which may be used for the preparation of the three-dimensional components as mouldings in a casting process. The tibial component of the endoprosthesis could be produced as a metallic part for being arranged on its associated joint bone and further of a separate plastic part which will receive an arrangement between this metallic part of the tibial component and an also metallic part defining the femoral component of the endoprosthesis. The same "Rapid Prototyping" may also be used for the preparation of corresponding STL patterns made, e.g., of epoxy resin and provided with those guiding slots at the marked severing areas which have been virtually transferred during the preceding step.

When an attending physician is held to consider a surgical intervention on a damaged knee joint the physician could then be provided with an operative set as oriented on the damaged knee joint and comprising femoral and tibial components of an endoprosthesis and femoral and tibial components of an associated implantation aid as prepared in accordance with the method according to the present invention. The operation of the patient will be carried out by first opening the knee joint and by subsequently severing the damaged components first at the tibia and then on the femoral bone. This particular severing will be carried out by using the implantation aid as a guide aid for guiding an oscillating sawing blade along the guiding slots of the implantation aid. The joint bones will thereby receive resection areas which exactly correspond with the severing areas as provided on the tibial and femoral components of the endoprosthesis of the particular operative set. These components may therefore be snugly fitted to the resection areas by means of the anchoring pegs which will be anchored in associated peg holes of the resection areas. When no anchoring means as e.g., such pegs coresponding peg holes are provided the components of the endoprosthrsis could then also be put together by any knows comenting method which will allow a correct seating of the components of the endoprosthesis prior to a final closing of the knee joint.

The preparation of the endoprosthesis could also include the preparation of a component which will be used for the patella of the damage knee joint. The method could further be also applied to surgical interventions of other joints such as for example of the ankle joint or of finger and toe joints and it could also be used for the reconstruction of bone and cartilage tissues as well as soft tissues.

BRIEF DESCRIPTION OF THE DRAWINGS

FIG. 5 illustrates schematically the femoral and tibial components of the endoprosthesis in accordance with and alternative embodiment and inducing pegs and associated pegs holes for allowings the components to be snugly fitter to the femoral bone and the tibia of the knee joint after its operation by use of the femoral and tibial components of the implantation and.

Figure 1:
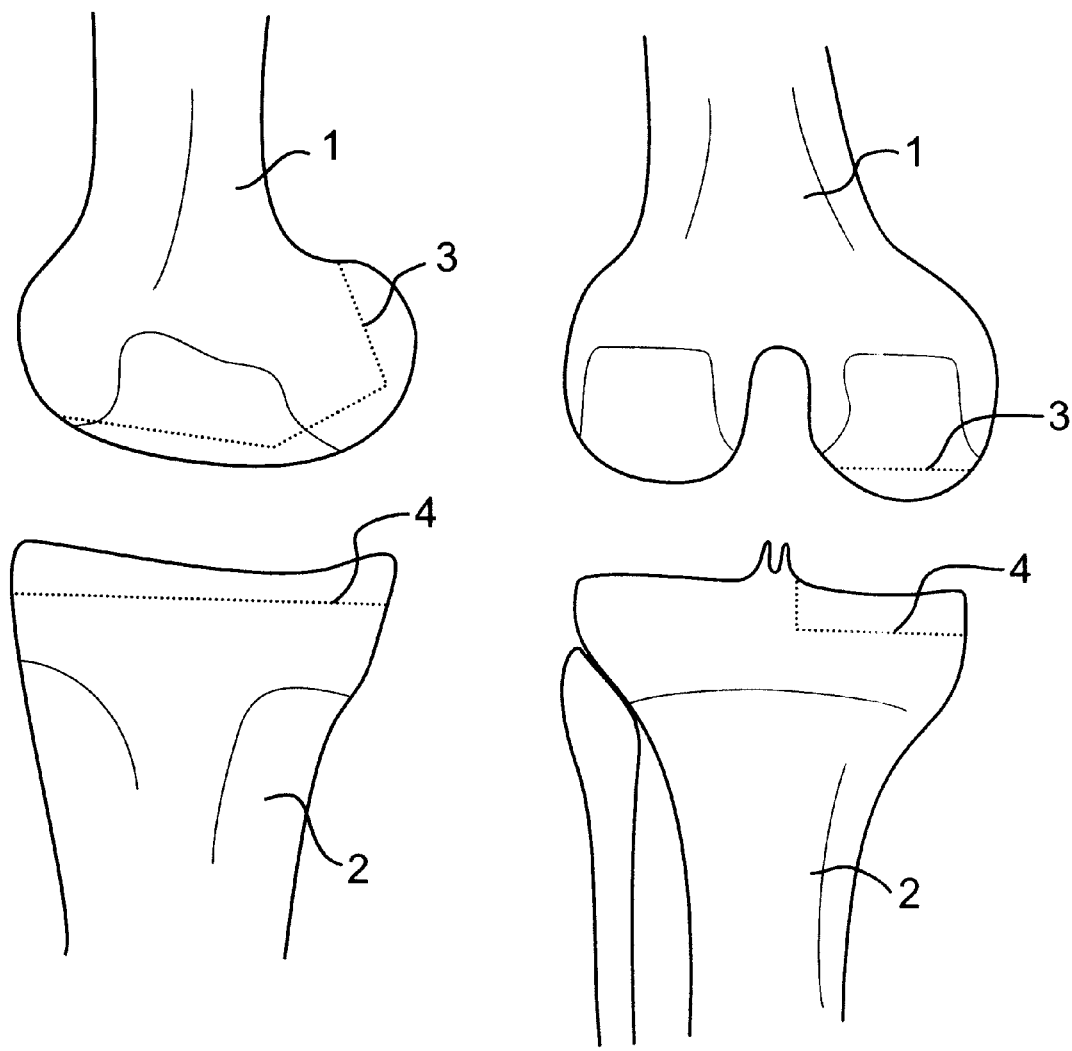
FIG. 1 illustrates schematically the step of preparing a preoparative tomographic image of a damaged kneejoin and the preparation of virtual severing areas for the damaged femoral and tibial components of the joint.
Figure 2:
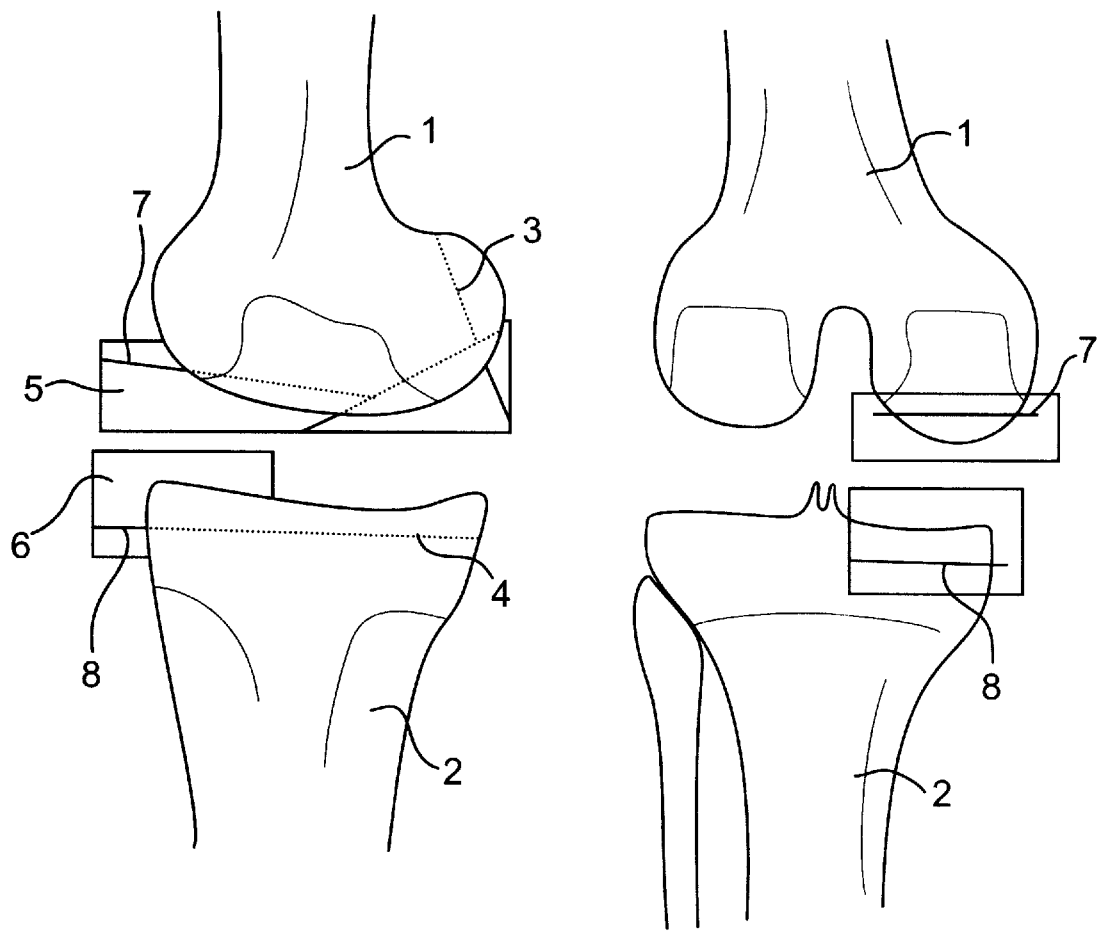
FIG. 2 illustrates schematically the virtual preparation tomographic images of femoral and tibial templates as visual patterns of an implantation aid whereby the severing areas are virtually transferred as virtual guiding slots of a guide aid for guiding an oscillating sawing blade during operation of the damaged knee joint.
Figure 3:
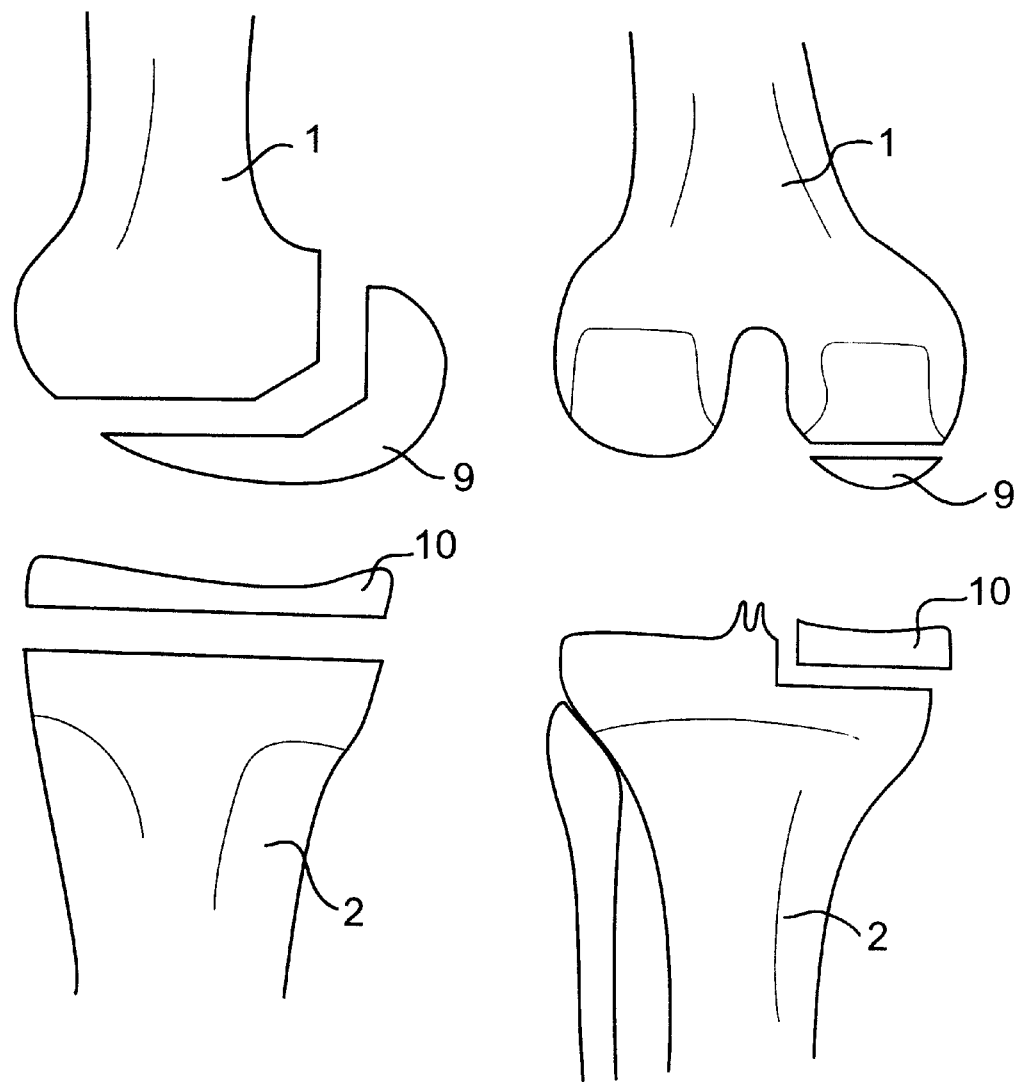
FIG. 3 illustrates schematically the virtual severing of femoral and tibial components of the damaged knee joint after having been virtually altered on the preoperative tomographic image for approximating the contours of the femoral bone and of the tibia of the damaged knee joint to those of a healthy knee joint.
Figure 4:
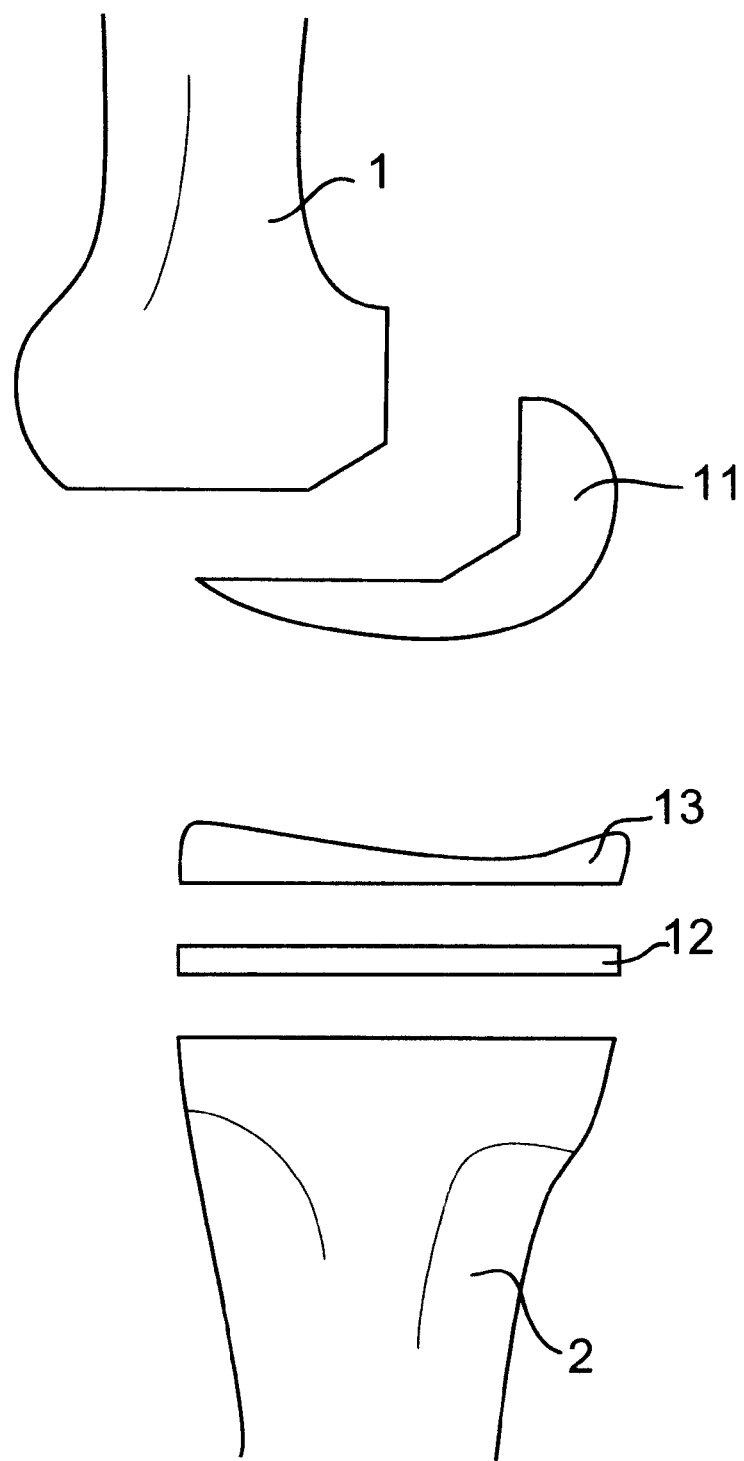
FIG. 4 illustrates schematically the three-dimensional femoral and tibia components of the endoprosthesis as prepared on the basis of their respective visual patterns.
Figure 5:
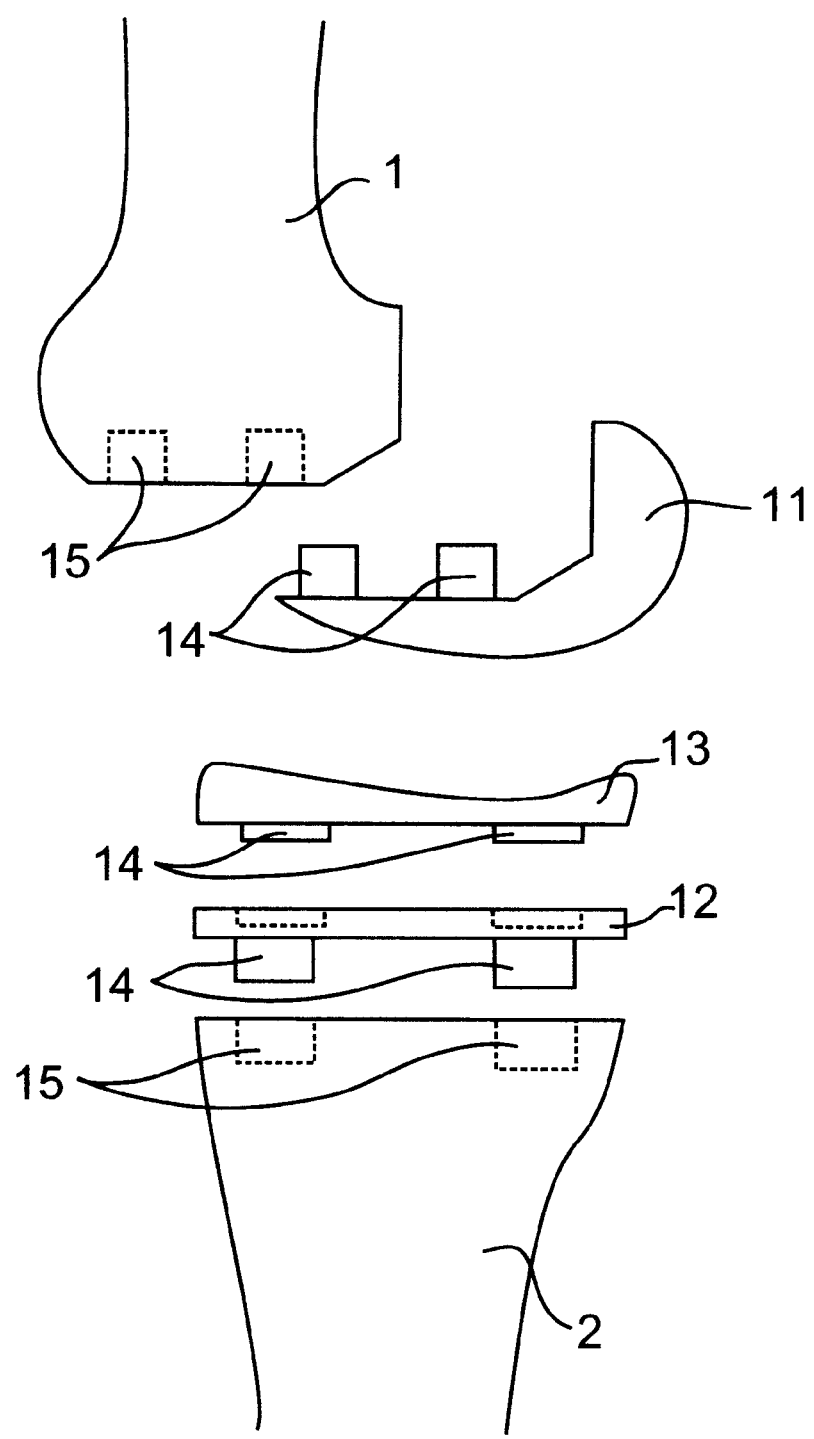

In the drawings, numerals 1 and 2 refer to the femoral bone and the tibia of a knee joint. Numerals 3 and 4 refer to the virtual severing areas as prepared on the preoperative tomographic image of a damaged knee joint which severing areas are virtualty transfered during a virtual preparation of tomographic images of femoral and tibia templates 5 and 6 for which the severing areas are exemplified as virtual guiding slots 7 and 8 of a guide aid. Numeral 9 and 10 refer to the femoral and tibial components of the damaged knee joint when severed virtually from the preoperative tomographicc image of the damaged knee joint after it has been virtually altered for approximating the contours of the femoral bone and of the tibia of the damaged knee joint to those of a healthy knee joint whereby these femoral and tibial components serve as visual patterns for the preparation of thee-dimensional femoral and tibial components of the endoprosthesis. Numerals 11, 12 and 13 refer to the components of the endoprosthesis which may be provided with pegs 14 that will fit snugly into peg holes 15 of the associated resection areas on the femoral bone 1 and of the tibia 2.

Although several embodiments of the present invention and its advantages have been described in detail, it should be understood that mutations, changes, substitution, transformations, modifications, variations and alterations can be made without departing from the teachings of the present invention, the spirit and scope of the invention being set forth by the appended claims.

We claim:

1. A method of producing an endoprosthesis as a joint substitute for knee joints comprising preparing a preoperative tomographic image of the damaged knee joint;

virtually altering the preoperative tomographic image for approximating the contours of at least the femoral bone and of the tibia of the damaged knee joint to those of a healthy knee joint;

virtually severing the altered femoral and tibial components defining respective components of a healthy knee joint as respectively visual patterns for the endoprosthesis whereby this severing is carried out on marked severing areas which later serve as thusly predetermined severing areas for severing the associated sociated components of the damaged knee joint from the joint bones during operation of the damaged knee joint;

virtually transferring the marked severing areas for virtually preparing tomographic images of a femoral and of a tibial template for the femoral and the tibial components of the damaged knee joint as respectively separate visual patterns of an implantation aid which fits snugly to the damaged knee joint whereby the severing areas when virtually transferred to the implantation aid are exemplified as virtual guiding slots of a guide aid for guiding an oscillating sawing blade during operation of the damaged knee joint when the damaged knee joint components are factually severed from the joint bones;

preparing three-dimensional femoral and tibial components of the endoprosthesis and three-dimensional femoral and tibial components of the associated implantation aid on the basis of their respective visual patterns.

2. The method of claim 1, wherein the altered femoral and tibial components defining respective components of a healthy knee joint are virtually supplemented on the marked severing areas with snugly fitting anchoring means for the three-dimensional components of the endoprosthesis when later fitted to the resection areas of the joint bones.

3. The method of claim 1, wherein the tomographic images are prepared by a computed tomography.

4. The method of claim 1, wherein the tomographic images are prepared by a nuclear spin resonance tomography.

5. The method of claim 1, wherein the step of virtually altering the preoperative tomographic image for defining a healthy knee joint is exemplified manually.

6. The method of claim 1, wherein the step of virtually altering the preoperative tomographic image for defining a healthy knee joint includes preparing a mirror image of a healthy knee joint of the patient.

7. The method of claim 1, wherein the step of virtually altering the preoperative tomographic image for defining a healthy knee joint includes identifying an image of a healthy knee joint having contours of at least the femoral bone and of the tibia comparable to the contours of the preoperative image of the damaged knee joint.

8. The method of claim 1, wherein the step of preparing the three-dimensional femoral and tibial components of the endoprosthesis and of the associated implantation aid includes digitizing the corresponding visual patterns and using the digitized visual patterns to prepare said components according to a copying process.

9. An operative set for carrying out operations on damaged knee joints, comprising femoral and tibial components of an endoprosthesis and femoral and tibial components of an associated implantation aid as produced in accordance with the method of claim 1.

10. The operative set of claim 9, wherein the femoral and tibial components of the endoprosthesis are provided with pegs which are intended for being fitted snugly into associated peg holes of the associated resection areas of the joint bones.

11. The operative set of claim 9, wherein the tibial component of the endoprosthesis comprises a plastic part and a metallic part of which the plastic part receives an arrangement between the metallic part of the tibial component and a corresponding metallic femoral component of the endoprosthesis.

* * * * *